US012611402B2

(12) United States Patent
Ramsden et al.

(10) Patent No.: US 12,611,402 B2
(45) Date of Patent: Apr. 28, 2026

(54) COMPOUNDS AND THEIR USE FOR THE TREATMENT OF ALPHA1-ANTITRYPSIN DEFICIENCY

(71) Applicant: CENTESSA PHARMACEUTICALS (UK) LIMITED, Altrincham (GB)

(72) Inventors: Nigel Ramsden, Cambridge (GB); David John Fox, Coventry (GB); James Andrew Huntington, Cheshire (GB); James Michael Tomlinson, Babraham (GB)

(73) Assignee: CENTESSA PHARMACEUTICALS (UK) LIMITED, Altrincham (GB)

(*) Notice: Subject to any disclaimer, the term of this patent is extended or adjusted under 35 U.S.C. 154(b) by 806 days.

(21) Appl. No.: 17/839,169

(22) Filed: Jun. 13, 2022

(65) Prior Publication Data

US 2023/0089087 A1 Mar. 23, 2023

Related U.S. Application Data

(63) Continuation of application No. PCT/GB2020/053187, filed on Dec. 11, 2020.

(30) Foreign Application Priority Data

Dec. 13, 2019 (GB) ..................................... 1918410

(51) Int. Cl.

| | |
|---|---|
| ***A61K 31/451*** | (2006.01) |
| ***A61K 31/4015*** | (2006.01) |
| ***A61K 31/4709*** | (2006.01) |
| ***A61P 1/16*** | (2006.01) |
| ***A61P 11/00*** | (2006.01) |

(52) U.S. Cl.

CPC ........ *A61K 31/451* (2013.01); *A61K 31/4015* (2013.01); *A61K 31/4709* (2013.01); *A61P 1/16* (2018.01); *A61P 11/00* (2018.01)

(58) Field of Classification Search

CPC .............. A61K 31/451; A61K 31/4015; A61K 31/4708

USPC ........................................................ 514/314

See application file for complete search history.

(56) References Cited

U.S. PATENT DOCUMENTS

| | | | | |
|---|---|---|---|---|
| 8,436,013 | B2 | 5/2013 | Liu et al. | |
| 9,084,782 | B2 | 7/2015 | Kwon et al. | |
| 2006/0035884 | A1 * | 2/2006 | Neitzel ................ | C07D 405/06 546/192 |
| 2011/0065707 | A1 | 3/2011 | Ackermann et al. | |
| 2020/0361939 | A1 | 11/2020 | Bandarage et al. | |
| 2024/0197707 | A1 | 6/2024 | Ramsden et al. | |

FOREIGN PATENT DOCUMENTS

| | | | |
|---|---|---|---|
| EP | 0520336 | A2 | 12/1992 |
| JP | H05345753 | A | 12/1993 |
| JP | 2007538106 | A | 12/2007 |
| JP | 2013504544 | A | 2/2013 |
| WO | WO-2005113542 | A2 | 12/2005 |
| WO | WO-2008143633 | A2 | 11/2008 |
| WO | WO-2011029808 | A1 | 3/2011 |
| WO | WO-2011110852 | A1 | 9/2011 |
| WO | WO-2018104220 | A1 | 6/2018 |
| WO | WO-2019243841 | A1 | 12/2019 |
| WO | WO-2020081257 | A1 | 4/2020 |
| WO | WO-2021116703 | A1 | 6/2021 |
| WO | WO-2022263816 | A1 | 12/2022 |

OTHER PUBLICATIONS

Elkins et al., "Variability in High-throughput Ion-Channel Screening Data and Consequences for Cardiac Safety Assessment," Journal of Pharmacological and Toxicological Methods 68:112-122 (2013).

Guidance for Industry. Estimating the Maximum Safe Starting Dose in Initial Clinical Trials for Therapeutics in Adult Healthy Volunteers, U.S. Department of Health and Human Services—FDA, Jul. 2005, Retrieved from the Internet: http://www.fda.gov/cder/guidance/index.html.

PCT/GB2022/051502 International Search Report and Written Opinion dated Aug. 17, 2022.

Weaver et al., "Cytochrome P450 Inhibition Using Recombinant Proteins and Mass Spectrometry/multiple Reaction Monitoring Technology in a Cassette Incubation," Drug Metabolism and Disposition 31(7):955-966 (2003).

Chemical Abstracts Service. CAS Registry: 1786870-80-1. STN Entry Date Jun. 23, 2015.

Chemical Abstracts Service. CAS Registry: 2649795-64-0. STN Entry Date Jul. 6, 2021.

Chemical Abstracts Service. CAS Registry: 727983-32-6. STN Entry Date Aug. 18, 2004.

Chemical Abstracts Service. CAS Registry: 891392-15-7. STN Entry Date Jul. 10, 2006.

Berthelier et al. Discovery of an Inhibitor of Z-Alpha1 Antitrypsin Polymerization. PLoS One 10(5):e0126256 (May 11, 2015).

Bouchecareilh et al. Histone deacetylase inhibitor (HDACi) suberoylanilide hydroxamic acid (SAHA)-mediated correction of α1-antitrypsin deficiency. J Biol Chem 287(45):38265-38278 (2012).

Burrows et al. Chemical chaperones mediate increased secretion of mutant alpha 1-antitrypsin (alpha 1-AT) Z: A potential pharmacological strategy for prevention of liver injury and emphysema in alpha 1-AT deficiency. PNAS USA 97(4):1796-1801 (2000).

Carlson et al. Accumulation of PiZ alpha 1-antitrypsin causes liver damage in transgenic mice. J. Clin Invest 83:1183-90 (1989).

Certified GB1918410.0, filed Dec. 13, 2019.

Chang et al. Small-molecule peptides inhibit Z alpha1-antitrypsin polymerization. J. Cell. Mol. Med. 13(8B):2304-2316 (2009).

(Continued)

*Primary Examiner* — Yevgeny Valenrod

(74) *Attorney, Agent, or Firm* — WILSON SONSINI GOODRICH & ROSATI

(57) ABSTRACT

The invention relates to specified carboxylic acid compounds of formula (1), and pharmaceutical compositions containing the compounds. The compounds may be inducers of $\alpha_1$-antitrypsin (A1AT) and may be used in the treatment of a disease or disorder such as $\alpha_1$-antitrypsin deficiency (A1AD or AATD).

17 Claims, 1 Drawing Sheet

(56) References Cited

OTHER PUBLICATIONS

Corral et al. Exploiting the Evolutionary Relationship between Malarial Parasites and Plants to Develop New Herbicides. Angew Chem Int Ed Engl 56(33):9881-9885 (2017).
Database accession No. 1394768-24-1, Chemical Abstracts Service (Sep. 18, 2012).
Database accession No. 1786658-64-7, Chemical Abstracts Service (Jun. 23, 2015).
Database accession No. 1786746-43-7, Chemical Abstracts Service (Jun. 23, 2015).
Database accession No. 1787438-88-3, Chemical Abstracts Service (Jun. 24, 2015).
Database accession No. 1840546-43-1, Chemical Abstracts Service (Jan. 3, 2016).
Database accession No. 630049-57-9, Chemical Abstracts Service (Dec. 23, 2003).
Database accession No. 727717-69-3, Chemical Abstracts Service (Aug. 17, 2004).
Database accession No. 891392-68-0, Chemical Abstracts Service (Jul. 10, 2006).
Dycaico et al. Neonatal hepatitis induced by alpha 1-antitrypsin: a transgenic mouse model. Science 242:1409-12 (1988).
Elliott et al. Topography of a 2.0 A structure of alpha1-antitrypsin reveals targets for rational drug design to prevent conformational disease. Protein Science 9:1274-1281 (2000).
GB1918410.0 Search Report dated Jun. 10, 2020.
Gould et al. Salt Selection for Basic Drugs. Int J. Pharm. 33:201-217 (1986).
Huntington. How and why the Z variant of a1-antitrypson polymerises, and what can be done about it. 7th International Symposium on Serpin Biology, Structure and Function (Apr. 1, 2014).
Knaupp et al. Kinetic instability of the serpin Z alpha1-antitrypsin promotes aggregation. J. Mol. Biol. 396:375-383 (2010).
Mallya et al. Small molecules block the polymerization of Z alpha1-antitrypsin and increase the clearance of intracellular aggregates. J Med Chem 50(22):5357-5363 (2007).
Parfrey et al. Targeting a surface cavity of alpha 1-antitrypsin to prevent conformational disease. J. Biol. Chem. 278(35):33060-33066 (2003).
PCT/GB2020/053187 International Search Report and Written Opinion dated Feb. 1, 2021.
Reddy et al. Synthesis and Antimicrobial screening of Some New Piperidine Derivatives. Journal of Applicable Chemistry 2(6):1501-1508 (2013).
Seyama et al. Siiyama (serine 53 (TCC) to phenylalanine 53 (TTC)). A new alpha 1-antitrypsin-deficient variant with mutation on a predicted conserved residue of the serpin backbone. J Biol Chem 266:12627-32 (1991).
Chemical Abstracts Service. CAS Registry: 1384659-27-1. 3-Pyrrolidinecarboxylic acid, 1-[[2-(trifluoromethyl)phenyl]sulfonyl]–,(3S)–. STN Entry Date Jul. 27, 2012.
Chemical Abstracts Service. CAS Registry: 1840546-43-1; Component RN 1384659-27-1. 3-Pyrrolidinecarboxylic acid, 1-[[2-(trifluoromethyl)phenyl]sulfonyl]–, hydrochloride (1:1). STN Entry Date Jan. 3, 2016.

* cited by examiner

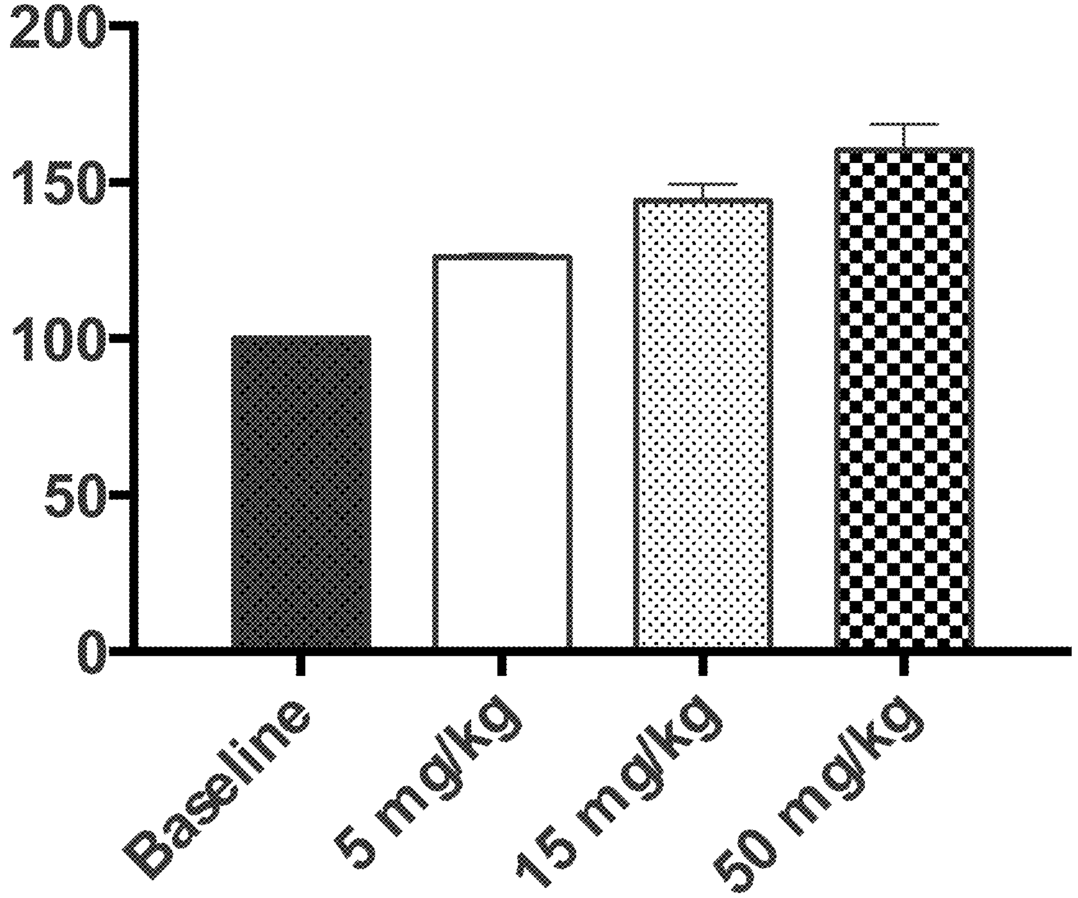
200
150
100
50
0
Baseline
5 mg/kg
15 mg/kg
50 mg/kg

COMPOUNDS AND THEIR USE FOR THE TREATMENT OF ALPHA1-ANTITRYPSIN DEFICIENCY

CROSS-REFERENCE

This application is the by-pass continuation of International Application No. PCT/GB2020/053187, filed Dec. 11, 2020, which claims the benefit of GB Application No. 1918410.0, filed Dec. 13, 2019, each of which are incorporated herein by reference in their entireties.

The invention relates to certain carboxylic acids and their medical use.

$\alpha_1$-Antitrypsin (A1AT) is a member of the serpin superfamily produced by the liver and secreted into the blood. It inhibits a variety of serine proteases, especially neutrophil elastase. When blood levels of A1AT are low, excessive neutrophil elastase activity degrades lung tissue resulting in respiratory complications, such as chronic obstructive pulmonary disease (COPD).

The reference range of A1AT in blood is 0.9-2.3 g/L. Levels lower than this are typical of $\alpha_1$-antitrypsin deficiency (A1AD or AATD), a genetic disorder caused by mutations in the SERPINA1 gene, coding for A1AT. The Z mutation, the most common cause of AATD, is the substitution of glutamate to lysine at position 366 of A1AT (UniProtKB-P01009 (A1AT_HUMAN)), corresponding to position 342 in the mature protein (Z A1AT). The Z mutation affects the folding of A1AT resulting in only a small fraction acquiring the native/active state. The remainder is either cleared as misfolded protein or accumulates in the liver as stable polymers. As a consequence of the misfolding, homozygous carriers of the Z mutation (ZZ) have plasma levels of A1AT that are 10-15% of normal, predisposing carriers to COPD. Accumulation of Z A1AT polymers in liver cells predisposes carriers to cirrhosis, liver cancer and other liver pathologies.

The current treatment for the lung manifestation of AATD involves augmentation therapy using A1AT concentrates prepared from the plasma of blood donors. The US FDA has approved the use of four A1AT products: Prolastin, Zemaira, Glassia, and Aralast. Dosing is via once weekly intravenous infusion. Augmentation therapy has been demonstrated to slow progression of COPD. The liver manifestations of AATD (e.g. cirrhosis and cancer) are treated with steroids and liver transplantation. Investigational approaches to improved treatment of the liver manifestations include inhibition of Z A1AT polymerisation and increased clearance of polymers through the activation of autophagy. Investigational approaches to improved treatment of both the lung and the liver manifestations are directed towards improvement of Z A1AT folding and secretion.

Elliott et al (Protein Science, 2000, 9, 1274-1281) have described an X-ray crystal structure of A1AT and identified five cavities that are potential targets for rational drug design to develop agents that will affect Z A1AT polymerisation.

Parfrey et al (J. Biol. Chem., 2003, 278, 35, 33060-33066) have further defined a single cavity that is a potential target for rational drug design to develop agents that will affect Z A1AT polymerisation.

Knaupp et al (J. Mol. Biol., 2010, 396, 375-383) have shown that bis-ANS (4,4'-dianilino-1,1'-binaphthyl-5,5'-disulfonate) is able to bind to Z A1AT but not to wild-type A1AT (M) with 1:1 stoichiometry and a $K_d$ of 700 nM.

Chang et al (J. Cell. Mol. Med., 2009, 13, 8B, 2304-2316) have reported a series of peptides, including Ac-TTAI-$NH_2$, that inhibit Z A1AT polymerization.

Burrows et al (Proc. Nat. Acad. Sci., 2000, 97, 4, 1796-1801) have shown that a series of non-selective chaperones, including 4-phenylbutyric acid, glycerol and trimethylamine oxide, are able to increase Z A1AT levels in cell supernatants and mouse models.

Bouchecareilh et al. (Journal of Biological Chemistry, 2012, 287, 45, 38265-38278) describe the use of histone deacetylase inhibitors, in particular SAHA (suberoylanilide hydroxamic acid) to increase the secretion of both wild type (M) and Z A1AT from cells.

Berthelier et al (PLOS ONE, May 11, 2015) have demonstrated that S-(4-nitrobenzyl)-6-thioguanosine is able to prevent Z A1AT polymerisation in vitro.

Mallya et al (J. Med. Chem., 2007, 50, 22, 5357-5363) describe a series of phenols, such as N-(4-hydroxy-3,5-dimethylphenyl)-2,5-dimethylthiophene-3-sulfonamide, able to block polymerisation of Z A1AT in vitro.

Huntington (XIIIth International Symposium on Proteinases, Inhibitors and Biological Control, 23 Sep. 2012, and 7th International Symposium on Serpin Biology, Structure and Function, 1 Apr. 2014) discussed a cavity from an X-ray crystal structure of Z A1AT that is a potential target for rational drug design to develop agents that will affect Z A1AT polymerisation.

U.S. Pat. No. 8,436,013B2 discloses a wide variety of structures able to increase secretion of Z A1AT from cells in the micromolar range.

Angewandte Chemie International Edition vol 56, no 33, 2017, 9881-9885 discloses 1-((4-chlorophenyl)sulfonyl)piperidine-4-carboxylic acid as a herbicide.

Journal of Applicable Chemistry vol 2, no 6, 2013, 1501-1508 discloses the synthesis of 1-(4-(trifluoromethyl) phenylsulfonyl)piperidine-4-carboxylic acid as an anti-bacterial agent.

US2011/0065707A1 discloses the use of 1-(2-chlorobenzene-sulfonyl)-piperidine-4-carboxylic acid as a reagent.

EP0520336A2 discloses 1-(8-quinoyl-sulfonyl)-piperidine-4-carboxylic acid.

WO2019/243841A1 discloses oxoindoline-4-carboxamide compounds as modulators of alpha-1-antitrypsin, and use in treating diseases associated with alpha-1-antitrypsin.

WO2020/081257A1 discloses pyrrolo-indazolyl-propanoic acid compounds as modulators of alpha-1-antitrypsin.

US2020/0361939A1 discloses further pyrrolo-indazolyl-propanoic acid compounds as modulators of alpha-1-antitrypsin.

A prior art search based on the structure of 1-((2-(trifluoromethyl)phenyl)sulfonyl)piperidine-3-carboxylic acid was conducted after the invention was made. The closest prior art molecule identified ex post facto by the search was the racemic compound, 1-((2-(trifluoromethyl)phenyl)sulfonyl) piperidine-3-carboxylic acid (CAS registry number 891392-68-0). This compound is listed as commercially available from Aurora, ChemDiv and the FCH Group but no publications are recorded. Another close prior art molecule is 1-(1-tosyl-1,2,5,6-tetrahydropyridin-3-yl)ethan-1-one (Example 16 in U.S. Pat. No. 9,084,782B2). The compound is stated to inhibit angiogenesis and lower cellular cholesterol levels (although no biological data are provided for this compound in U.S. Pat. No. 9,084,782B2).

According to one aspect of the present invention, there is provided a compound (a carboxylic acid) of formula (1):

(I)

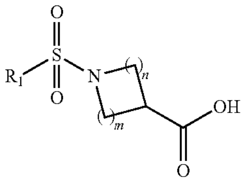

where

R$_1$ is an optionally substituted or fused aryl or heteroaryl ring system, m and n are independently 1, 2 or 3, but the combination where both n and m are 1 is excluded, when the combination of m and n results in a chiral centre, optionally both enantiomers and the racemic mixture are included, and the compound is 1-(Quinolin-8-ylsulfonyl)piperidine-4-carboxylic acid or 1-((2-Chlorophenyl)sulfonyl)piperidine-4-carboxylic acid or 1-((3-Chlorophenyl)sulfonyl)piperidine-4-carboxylic acid or 1-((2,3-Dichlorophenyl)sulfonyl)piperidine-4-carboxylic acid or (S)-1-((3-Fluorophenyl)sulfonyl)piperidine-3-carboxylic acid or (S)-1-((3-Chlorophenyl)sulfonyl)piperidine-3-carboxylic acid or (R)-1-((3-Fluorophenyl)sulfonyl)piperidine-3-carboxylic acid or (R)-1-((3-Chlorophenyl)sulfonyl)piperidine-3-carboxylic acid or 1-((4-Chlorophenyl)sulfonyl)piperidine-4-carboxylic acid or 1-((2-(Trifluoromethyl)phenyl)sulfonyl)piperidine-4-carboxylic acid or 1-((3-(Trifluoromethyl)phenyl)sulfonyl)piperidine-4-carboxylic acid or 1-((4-(Trifluoromethyl)phenyl)sulfonyl)piperidine-4-carboxylic acid or 1-((2,5-Bis(trifluoromethyl)phenyl)sulfonyl)piperidine-4-carboxylic acid or 1-((2-(Trifluoromethoxy)phenyl)sulfonyl)piperidine-4-carboxylic acid or (S)-1-((2-(Trifluoromethyl)phenyl)sulfonyl)pyrrolidine-3-carboxylic acid or (R)-1-((2-(Trifluoromethyl)phenyl)sulfonyl)pyrrolidine-3-carboxylic acid or (S)-1-((2-(Trifluoromethyl)phenyl)sulfonyl)piperidine-3-carboxylic acid or (R)-1-((2-(Trifluoromethyl)phenyl)sulfonyl)piperidine-3-carboxylic acid.

We have found that compounds of the invention are shown surprisingly to be highly effective at increasing levels of correctly folded, and hence active, Z A1AT, whilst having no effect on the secretion of wild type (M) A1AT or of the Siiyama variant of A1AT.

Also provided according to the invention is a mixture of the two enantiomers of any compound according to claim 1 which has a chiral centre, where the mixture is either racemic or has one enantiomer in excess of the other enantiomer.

The compound or mixture of the invention may be in a pharmaceutically acceptable salt form or crystalline form.

The term "pharmaceutically acceptable salt" refers to a pharmaceutically acceptable mono organic or inorganic salt of the compound of the invention. This may include those derived from bases such as sodium hydroxide, potassium hydroxide, lithium hydroxide, calcium hydroxide, 1-deoxy-2-(methylamino)-D-glucitol, magnesium hydroxide, zinc hydroxide, aluminium hydroxide, ferrous or ferric hydroxide, ammonium hydroxide or organic amines such as N-methylglucamine, choline, arginine and the like. For other examples of pharmaceutically acceptable salts, reference can be made to Gould (1986, Int J Pharm 33: 201-217).

According to a further aspect of the invention, there is a provided a pharmaceutical composition comprising the compound or mixture of the invention as described herein and a pharmaceutically or therapeutically acceptable excipient or carrier.

The term "pharmaceutically or therapeutically acceptable excipient or carrier" refers to a solid or liquid filler, diluent or encapsulating substance which does not interfere with the effectiveness or the biological activity of the active ingredients and which is not toxic to the host, which may be either humans or animals, to which it is administered. Depending upon the particular route of administration, a variety of pharmaceutically acceptable carriers such as those well known in the art may be used. Non-limiting examples include sugars, starches, cellulose and its derivatives, malt, gelatin, talc, calcium sulfate, vegetable oils, synthetic oils, polyols, alginic acid, phosphate buffered solutions, emulsifiers, isotonic saline, and pyrogen-free water.

All suitable modes of administration are contemplated according to the invention. For example, administration of the medicament may be via oral, subcutaneous, direct intravenous, slow intravenous infusion, continuous intravenous infusion, intravenous or epidural patient controlled analgesia (PCA and PCEA), intramuscular, intrathecal, epidural, intracistemal, intraperitoneal, transdermal, topical, transmucosal, buccal, sublingual, transmucosal, inhalation, intranasal, intra-atricular, intranasal, rectal or ocular routes. The medicament may be formulated in discrete dosage units and can be prepared by any of the methods well known in the art of pharmacy.

All suitable pharmaceutical dosage forms are contemplated. Administration of the medicament may for example be in the form of oral solutions and suspensions, tablets, capsules, lozenges, effervescent tablets, transmucosal films, suppositories, buccal products, oral mucoretentive products, topical creams, ointments, gels, films and patches, transdermal patches, abuse deterrent and abuse resistant formulations, sterile solutions suspensions and depots for parenteral use, and the like, administered as immediate release, sustained release, delayed release, controlled release, extended release and the like.

Another aspect of the invention is the use of the compound or mixture of the invention as defined herein in the manufacture of a medicament for the treatment of a disease or disorder.

A further aspect of the invention is the compound or mixture of the invention for use as an inducer of Z A1AT secretion.

Further provided is the compound or mixture of the invention as defined herein for use in the treatment of a disease or disorder.

The invention also encompasses a method of treating a disease or disorder, comprising the step of administering the compound or mixture or the pharmaceutical composition of the invention as defined herein to a patient in need of same.

The invention further encompasses the use of a compound or mixture of the invention as an inducer of Z A1AT secretion. The use may be in the treatment of a disease or disorder. Additionally or alternatively, the use may be in vitro, for example in an in vitro assay.

A disease or disorder suitable for treatment according to the relevant aspects of the invention is one which is characterised by low plasma levels of A1AT, for example AATD.

The invention also provides the use of a racemic compound of formula (1) in the manufacture of a medicament for the treatment of a disease or disorder, wherein the disease or disorder is AATD.

Also provided is the use of a racemic compound of formula (1) as an inducer of Z A1AT secretion.

The use of a numerical range in this description is intended unambiguously to include within the scope of the invention all individual integers within the range and all the combinations of upper and lower limit numbers within the broadest scope of the given range.

As used herein, the term “comprising” is to be read as meaning both comprising and consisting of. Consequently, where the invention relates to a “pharmaceutical composition comprising as active ingredient” a compound, this terminology is intended to cover both compositions in which other active ingredients may be present and also compositions which consist only of one active ingredient as defined.

Unless otherwise defined, all the technical and scientific terms used here have the same meaning as that usually understood by an ordinary specialist in the field to which this invention belongs. Similarly, all the publications, patent applications, all the patents and all other references mentioned here are incorporated by way of reference in their entirety (where legally permissible).

Particular non-limiting examples of the present invention will now be described.

FIG. 1 is a graph showing the effect of (S)-1-((2-(trifluoromethyl)phenyl)sulfonyl)piperidine-3-carboxylic acid on Z A1AT levels in mice expressing human Z A1AT (huZ mice). Mice were treated with vehicle, 5, 15 and 50 mg/kg of (S)-1-((2-(trifluoromethyl)phenyl)sulfonyl)piperidine-3-carboxylic acid twice a day by oral gavage for 14 consecutive days. Blood was taken on days −12, −7 and −5 and plasma prepared to determine circulating basal levels of human Z A1AT. Plasma samples collected the last three days of the study (days 12, 13 and 14) were used to determine the effect of (S)-1-((2-(trifluoromethyl)phenyl)sulfonyl)piperidine-3-carboxylic acid treatment on circulating human Z A1AT levels compared to basal levels. The x-axis is the treatment dose of (S)-1-((2-(trifluoromethyl)phenyl)sulfonyl)piperidine-3-carboxylic acid in mg/kg; the y-axis is the mean percentage level of human Z A1AT compared to baseline levels for each treatment group (i.e. A1AT % Baseline).

EXPERIMENTAL

General Method

Compounds of formula 1 were prepared using the following synthetic procedure.

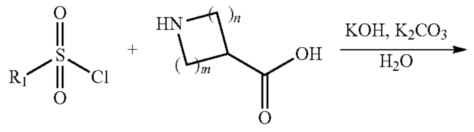

-continued

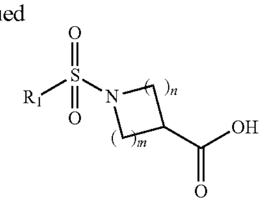

The carboxylic acid (1 equivalent), potassium hydroxide (1 equivalent) and potassium carbonate (2 equivalents) were added to water and stirred. The sulfonyl chloride (1 equivalent) was added and the reaction was stirred at room temperature for 3 hours. The reaction was cooled to 0° C. and acidified with 2M hydrochloric acid to give a white precipitate. This precipitate was dried and triturated with n-pentane to give the compound of formula (1).

Example 1: 1-(Quinolin-8-ylsulfonyl)piperidine-4-carboxylic acid

The compound of Example 1 was prepared using the general method and 1-quinolin-8-ylsulfonylchloride and piperidine-4-carboxylic acid.

$^1$H NMR (400 MHz, d6 DMSO) δ 12.26 (1H, s), 9.07 (OH, s), 8.54 (1H, d), 8.36 (1H, d), 8.30 (1H, d), 7.74 (1H, m), 7.70 (OH, m), 3.81 (2H, m), 2.82 (2H, m), 2.31 (1H, m), 1.82 (2H, m), 1.44 (0H, m).

Example 2: 1-((2-Chlorophenyl)sulfonyl)piperidine-4-carboxylic acid

The compound of Example 2 was prepared using the general method and 1-(2-chlorophenyl)sulfonylchloride and piperidine-4-carboxylic acid.

$^1$H NMR (400 MHz, d6 DMSO) δ 12.38 (1H, br s), 7.97 (1H, d), 7.88 (2H, m), 7.56 (1H, m), 3.60 (2H, m), 2.83 (2H, t), 2.40 (1H, m), 1.86 (2H, m), 1.48 (2H, m).

Example 3: 1-((3-Chlorophenyl)sulfonyl)piperidine-4-carboxylic acid

The compound of Example 3 was prepared using the general method and 1-(3-chlorophenyl)sulfonylchloride and piperidine-4-carboxylic acid.

$^1$H NMR (400 MHz, $CDCl_3$) δ 7.77 (1H, s), 7.76 (1H, d), 7.63 (1H, m), 7.60 (1H, m), 3.68 (2H, m), 2.55 (2H, t), 2.37 (1H, m), 2.02 (2H, m), 1.86 (2H, m).

Example 4: 1-((2,3-Dichlorophenyl)sulfonyl)piperidine-4-carboxylic acid

The compound of Example 4 was prepared using the general method and 1-(2,3-dichlorophenyl)sulfonylchloride and piperidine-4-carboxylic acid.

$^1$H NMR (400 MHz, d6 DMSO) δ 12.36 (1H, br s), 7.97 (2H, d), 7.59 (1H, m), 3.64 (2H, m), 2.90 (2H, t), 2.43 (1H, m), 1.80 (2H, m), 1.54 (2H, m).

Example 5: (S)-1-((3-Fluorophenyl)sulfonyl)piperidine-3-carboxylic acid

The compound of Example 5 was prepared using the general method and 1-(3-fluorophenyl)sulfonylchloride and (S)-piperidine-3-carboxylic acid.

$^1H$ NMR (400 MHz, $CD_3OD$) δ 7.52 (2H, m), 7.48 (1H, m), 7.44 (1H, m), 3.73 (1H, d), 3.53 (1H, d), 2.60 (3H, m), 1.97 (1H, m), 1.81 (1H, m), 1.59 (1H, m), 1.50 (1H, m).

Example 6: (S)-1-((3-Chlorophenyl)sulfonyl)piperidine-3-carboxylic acid

The compound of Example 6 was prepared using the general method and 1-(3-chlorophenyl)sulfonylchloride and (S)-piperidine-3-carboxylic acid.

$^1H$ NMR (400 MHz, $CD_3OD$) δ 7.79 (1H, s), 7.68 (2H, m), 7.62 (1H, m), 3.72 (1H, d), 3.51 (1H, d), 2.60 (3H, m), 1.97 (1H, m), 1.81 (1H, m), 1.58 (1H, m), 1.51 (1H, m).

Example 7: (R)-1-((3-Fluorophenyl)sulfonyl)piperidine-3-carboxylic acid

The compound of Example 7 was prepared using the general method and 1-(3-fluorophenyl)sulfonylchloride and (R)-piperidine-3-carboxylic acid.

$^1H$ NMR (400 MHz, $CD_3OD$) δ 7.52 (2H, m), 7.48 (1H, m), 7.44 (1H, m), 3.73 (1H, d), 3.53 (1H, d), 2.60 (3H, m), 1.97 (1H, m), 1.81 (1H, m), 1.59 (1H, m), 1.50 (1H, m).

Example 8: (R)-1-((3-Chlorophenyl)sulfonyl)piperidine-3-carboxylic acid

The compound of Example 8 was prepared using the general method and 1-(3-chlorophenyl)sulfonylchloride and (R)-piperidine-3-carboxylic acid.

$^1H$ NMR (400 MHz, $CD_3OD$) δ 7.79 (1H, s), 7.68 (2H, m), 7.62 (1H, m), 3.73 (1H, d), 3.53 (1H, d), 2.60 (3H, m), 1.97 (1H, m), 1.81 (1H, m), 1.59 (1H, m), 1.50 (1H, m).

Example 9: 1-((4-Chlorophenyl)sulfonyl)piperidine-4-carboxylic acid

The compound of Example 9 was prepared using the general method and 1-(4-chlorophenyl)sulfonylchloride and piperidine-4-carboxylic acid.

$^1H$ NMR (400 MHz, d6 DMSO) δ 12.32 (1H, s), 7.73 (4H, m), 3.47 (2H, m), 2.44 (2H, m), 2.28 (1H, m), 1.86 (2H, m), 1.57 (2H, m).

Example 10: 1-((2-(Trifluoromethyl)phenyl)sulfonyl)piperidine-4-carboxylic acid

The compound of Example 10 was prepared using the general method and 1-(2-(trifluoromethyl)phenyl)sulfonylchloride and piperidine-4-carboxylic acid.

$^1H$ NMR (400 MHz, d6 DMSO) δ 12.36 (1H, s), 8.03 (2H, m), 7.90 (2H, m), 3.61 (2H, m), 2.85 (2H, m), 2.41 (1H, m), 1.90 (2H, m), 1.55 (2H, m).

Example 11: 1-((3-(Trifluoromethyl)phenyl)sulfonyl)piperidine-4-carboxylic acid

The compound of Example 11 was prepared using the general method and 1-(3-(trifluoromethyl)phenyl)sulfonylchloride and piperidine-4-carboxylic acid.

$^1H$ NMR (400 MHz, d6 DMSO) δ 12.33 (1H, s), 8.13 (1H, m), 8.07 (1H, m), 7.95 (1H, m), 7.90 (1H, m), 3.53 (2H, m), 2.45 (2H, m), 2.32 (1H, m), 1.89 (2H, m), 1.57 (2H, m).

Example 12: 1-((4-(Trifluoromethyl)phenyl)sulfonyl)piperidine-4-carboxylic add

The compound of Example 12 was prepared using the general method and 1-(4-(trifluoromethyl)phenyl)sulfonylchloride and piperidine-4-carboxylic acid.

$^1H$ NMR (400 MHz, d6 DMSO) δ 8.00 (2H, m), 7.92 (2H, m), 3.20 (2H, m), 2.54 (2H, m), 1.70 (3H, m), 1.57 (2H, m).

Example 13: 1-((2,5-Bis(trifluoromethyl)phenyl)sulfonyl)piperidine-4-carboxylic acid The compound of Example 13 was prepared using the general method and 1-(2,5-bis(trifluoromethyl)phenyl)sulfonylchloride and piperidine-4-carboxylic acid.

$^1H$ NMR (400 MHz, d6 DMSO) δ 12.36 (1H, s), 8.30 (2H, m), 8.24 (1H, s), 3.65 (2H, m), 2.87 (2H, m), 2.43 (1H, m), 1.89 (2H, m), 1.54 (2H, m).

Example 14: 1-((2-(Trifluoromethoxy)phenyl)sulfonyl)piperidine-4-carboxylic acid The compound of Example 14 was prepared using the general method and 1-(2-(trifluoromethoxy)phenyl)sulfonylchloride and piperidine-4-carboxylic acid.

$^1H$ NMR (400 MHz, d6 DMSO) δ 12.33 (1H, s), 7.93 (1H, m), 7.83 (1H, m), 7.62 (2H, m), 3.56 (2H, m), 2.71 (2H, m), 2.36 (1H, m), 1.87 (2H, m), 1.52 (2H, m).

Example 15: (S)-1-((2-(Trinfluoromethyl)phenyl)sulfonyl)pyrrolidine-3-carboxylic acid The compound of Example 15 was prepared using the general method and 1-(2-(trifluoromethyl)phenyl)sulfonylchloride and (S)-pyrrolidine-3-carboxylic acid.

$^1H$ NMR (400 MHz, d6 DMSO) δ 12.62 (1H, br s), 8.05 (2H, m), 7.90 (2H, m), 3.48 (2H, m), 3.38 (2H, m), 3.15 (1H, m), 2.11 (2H, m).

Example 16: (R)-1-((2-(Trifluoromethyl)phenyl)sulfonyl)pyrrolidine-3-carboxylic acid The compound of Example 16 was prepared using the general method and 1-(2-(trifluoromethyl)phenyl)sulfonylchloride and (R)-pyrrolidine-3-carboxylic acid $^1H$ NMR (400 MHz, d6 DMSO) δ 12.62 (1H, br s), 8.05 (2H, m), 7.90 (2H, m), 3.48 (2H, m), 3.38 (2H, m), 3.15 (1H, m), 2.11 (2H, m).

Example 17: (S)-1-((2-(Trinfluoromethyl)phenyl)sulfonyl)piperidine-3-carboxylic acid (S)-1-((2-(Trifluoromethyl)phenyl)sulfonyl)piperidine-3-carboxylic acid was prepared using the following synthesis procedure.

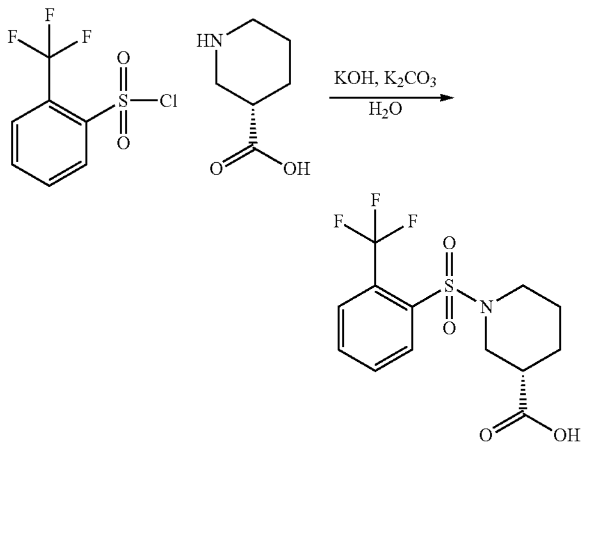

(S)-Piperidine-3-carboxylic acid (1 g, 7.7 mmol), potassium hydroxide (434 mg, 7.7 mmol) and potassium carbonate (2.14 g, 15.4 mmol) were added to water (20 ml) and stirred. 2-(Trifluoromethyl)benzenesulfonyl chloride (1.89 g, 7.7 mmol) was added and the reaction was stirred at room temperature for 3 hours. The reaction was cooled to 0° C. and acidified with 2M hydrochloric acid to give a white precipitate. This precipitate was dried and triturated with n-pentane to give (S)-1-((2-(trifluoromethyl)phenyl)sulfonyl)piperidine-3-carboxylic acid.

Tlc Rf 0.3 70% ethyl acetate in hexane.

m/z: 337.98 (calc 338.03)

$^1$H NMR (400 MHz, d6 DMSO) δ 12.33 (1H, s), 8.04 (2H, m), 7.90 (2H, m), 3.69 (1H, dd), 3.50 (1H, dd), 2.93 (1H, m), 2.81 (1H, m), 1.91 (1H, m), 1.72 (1H, m), 1.50 (2H, m).

Example 18: (R)-1-((2-(Trifluoromethyl)phenyl)sulfonyl)piperidine-3-carboxylic acid (R)-1-((2-(Trifluoromethyl)phenyl)sulfonyl)piperidine-3-carboxylic acid was prepared in the same manner as (S)-1-((2-(trifluoromethyl)phenyl)sulfonyl)piperidine-3-carboxylic acid, but using (R)-piperidine-3-carboxylic acid.

Tlc Rf 0.3 70% ethyl acetate in hexane.

m/z: 338.03 (calc 338.03)

1H NMR (400 MHz, d6 DMSO) δ 12.53 (1H, s), 8.04 (2H, m), 7.90 (2H, m), 3.69 (1H, dd), 3.49 (1H, dd), 2.93 (1H, m), 2.81 (1H, m), 1.90 (1H, m), 1.72 (1H, m), 1.49 (2H, m).

Example 19: Activity of the Compounds of Examples 1-18 in an A1AT Cell Secretion Assay Using HEK-Z Cells Methods HEK-Z cells, a human embryonic kidney cell line stably transfected with the human Z A1AT gene, were plated into 96 well plates ($3.0\times10^5$ cells/ml with 200 μl of media/well) overnight at 37° C. in a humidified atmosphere containing 5% $CO_2$. Following incubation cells were washed with 200 μl serum-free media three times and media was replaced with treatments in quadruplicate using serum-free media containing vehicle, 10 μM suberanilohydroxamic acid (SAHA) or the compounds of Examples 1-18 (at concentrations of 10, 33, 100 and 333 nM) for 48 h in a 37° C. incubator in a final volume of 200 μl. At the end of the incubation step the supernatants were removed from the wells, centrifuged at 1000×g at 4° C. for 10 min and were assayed for human A1AT levels by ELISA (Human Serpin A1/$\alpha_1$-antitrypsin duo set ELISA, R& D Systems, DY1268) per manufacturer's instructions.

Briefly, a 96 well plate was coated with human A1AT capture antibody overnight at room temperature (1:180 dilution from stock, 100 μl final volume/well). The capture antibody was then removed and wells washed three times with 300 μl wash buffer (0.05% Tween 20 in PBS) and then 200 μl reagent diluent (25% Tween 20 in PBS) was incubated in each well for 1 h at room temperature. Diluted samples, standards (125, 250, 500, 1000, 2000, 4000 and 8000 pg/ml A1AT) or blanks were then added to each well in duplicate and the plates were covered with a plate sealer and left at room temperature for 2 h. At the end of the sample incubation step, samples were removed and all wells washed as previously and 100 μl detection antibody (1:180 dilution from stock) was added to each well and incubated for a further 2 h at room temperature. Following incubation with detection antibody, supernatant was removed and wells were washed as previously and 100 μl streptavidin-HRP solution (1:200 dilution from stock) was added to each well for 20 min in the dark. After which, 50 μl stop solution (2M $H_2SO_4$) was added and optical density (OD) of each well was read at 450 nm with 570 nm blank subtracted from each well using a microplate reader. A 4 parameter logistic curve was constructed using GraphPad Prism 7 and A1AT concentrations were determined in each sample by interpolation from a standard curve and multiplying by the appropriate dilution factor.

Results

The amount of human A1AT secreted from transfected HEK-EBNA cells into the media was measured by ELISA. SAHA at 10 μM was used a positive control for all in vitro A1AT secretion experiments.

The data in Table 1 show that the compounds of Examples 1-18 increase the secretion of human Z A1AT from HEK-Z cells in a dose dependent manner as measured by ELISA.

TABLE 1

| Example | Median A1AT increase over vehicle at 300 nM |
|---|---|
| 1 | 247 |
| 2 | 235 |
| 3 | 166 |
| 4 | 147 |
| 5 | 220 |
| 6 | 240 |
| 7 | 280 |
| 8 | 260 |
| 9 | 200 |
| 10 | 235 |
| 11 | 215 |
| 12 | 200 |
| 13 | 213 |
| 14 | 227 |
| 15 | 230 |
| 16 | 200 |
| 17 | 310 |
| 18 | 200 |

Example 20: Activity of the Compounds of Examples 1-18 in an A1AT Cell Secretion Assay Using HEK-M Cells Methods HEK-M cells, a human embryonic kidney cell line stably transfected with M A1AT, were plated into 96 well plates ($3.0\times10^5$ cells/ml with 200 μl of media/well) overnight at 37° C. in a humidified atmosphere containing 5% $CO_2$. Following incubation cells were washed with 200 μl serum-free media three times and media was replaced with serum-free media containing vehicle, 10 μM suberanilohydroxamic acid (SAHA) or a compound of Examples 1-16 in replicates of six for 48 h in a 37° C. incubator in a final volume of 200 μl. At the end of the incubation step the supernatants were removed from the wells, centrifuged at 1000×g at 4° C. for 10 min and were assayed for human A1AT levels by ELISA (Human Serpin A1/$\alpha_1$ antitrypsin duo set ELISA, R& D Systems, DY1268) per manufacturer's instructions.

Briefly, a 96 well plate was coated with human A1AT capture antibody overnight at room temperature (1:180 dilution from stock, 100 μl final volume/well). The capture antibody was then removed and wells washed three times with 300 μl wash buffer (0.05% Tween 20 in PBS) and then 200 μl reagent diluent (25% Tween 20 in PBS) was incubated in each well for 1 h at room temperature. Diluted samples, standards (125, 250, 500, 1000, 2000, 4000 and 8000 pg/ml A1AT) or blanks were then added to each well in duplicate and the plates were covered with a plate sealer and left at room temperature for 2 h. At the end of the sample incubation step, samples were removed and all wells washed as previously and 100 µl detection antibody (1:180 dilution from stock) was added to each well and incubated for a further 2 h at room temperature. Following incubation with detection antibody, supernatant was removed and wells were washed as previously and 100 µl streptavidin-HRP solution (1:200 dilution from stock) was added to each well for 20 min in the dark. After which, 50 µl stop solution (2M $H_2SO_4$) was added and optical density (OD) of each well was read at 450 nm with 570 nm blank subtracted from each well using a microplate reader. A 4 parameter logistic curve was constructed using GraphPad Prism 7 and A1AT concentrations were determined in each sample by interpolation from a standard curve and multiplying by the appropriate dilution factor.

Results

The amount of human M A1AT secreted from transfected HEK-EBNA cells into the media was measured by ELISA. SAHA at 10 µM was used a positive control for all in vitro A1AT secretion experiments. The compounds of Examples 1, 3, 4, 10, 17 and 18 did not lead to an increase in secretion of human M A1AT from HEK-M cells at 10 µM.

Example 21: Activity of the Compounds of Examples 1 and 17 in an A1AT Cell Secretion Assay Using HEK-Siiyama Cells The rare Siiyama mutation (Ser 53 to Phe, mature A1AT numbering) was identified in a Japanese male with AATD (Seyama et al J Biol Chem (1991) 266:12627-32). Ser53 is one the conserved serpin residues and is thought to be important for the organization of the internal core of the A1AT molecule. The change from an uncharged polar to a large nonpolar amino acid on the conserved backbone of the protein affects the folding and intracellular processing of Siiyama A1AT.

Methods

HEK-Siiyama cells, a human embryonic kidney cell line stably transfected with the human Siiyama A1AT gene, were plated into 96 well plates ($3.0\times10^5$ cells/ml with 200 µl of media/well) overnight at 37° C. in a humidified atmosphere containing 5% $CO_2$. Following incubation cells were washed with 200 µl serum-free media three times and media was replaced with serum-free media containing vehicle, 10 µM suberanilohydroxamic acid (SAHA) or a compound of Example 1 (at 1 and 10 µM) in replicates of eight for 48 h in a 37° C. incubator in a final volume of 200 µl. At the end of the incubation step the supernatants were removed from the wells, centrifuged at 1000×g at 4° C. for 10 min and were assayed for human A1AT levels by ELISA (Human Serpin A1/$\alpha_1$-antitrypsin duo set ELISA, R& D Systems, DY1268) per manufacturer's instructions.

Briefly, a 96 well plate was coated with human A1AT capture antibody overnight at room temperature (1:180 dilution from stock, 100 µl final volume/well). The capture antibody was then removed and wells washed three times with 300 µl wash buffer (0.05% Tween 20 in PBS) and then 200 µl reagent diluent (25% Tween 20 in PBS) was incubated in each well for 1 h at room temperature. Diluted samples, standards (125, 250, 500, 1000, 2000, 4000 and 8000 pg/ml A1AT) or blanks were then added to each well in duplicate and the plates were covered with a plate sealer and left at room temperature for 2 h. At the end of the sample incubation step, samples were removed and all wells washed as previously and 100 µl detection antibody (1:180 dilution from stock) was added to each well and incubated for a further 2 h at room temperature. Following incubation with detection antibody, supernatant was removed and wells were washed as previously and 100 µl streptavidin-HRP solution (1:200 dilution from stock) was added to each well for 20 min in the dark. After which, 50 µl stop solution (2M $H_2SO_4$) was added and optical density (OD) of each well was read at 450 nm with 570 nm blank subtracted from each well using a microplate reader. A 4 parameter logistic curve was constructed using GraphPad Prism 7 and A1AT concentrations were determined in each sample by interpolation from a standard curve and multiplying by the appropriate dilution factor.

Results

The amount of human Siiyama A1AT secreted from transfected HEK-EBNA cells into the media was measured by ELISA. SAHA at 10 µM was used a positive control for all in vitro A1AT human secretion experiments. The exemplar compounds of Example 1 and 17 did not stimulate secretion of Siiyama A1AT from HEK-Siiyama cells at 1 or 10 µM, as measured by ELISA. In contrast, the positive control 10 µM SAHA stimulated an increase in Siiyama A1AT secretion.

Example 22: Activity of the Compounds of Examples 1 and 17 in a Mouse Expressing Human Z (huZ Mouse)

The huZ mouse (also referred to as the PiZZ mouse) is a transgenic mouse strain that contains multiple copies of the Z variant of the human A1AT gene, developed by two separate groups (Dycaico et al Science (1988) 242:1409-12) and Carlson et al J. Clin Invest (1989) 83:1183-90). HuZ mice are on a C57Bl/6 background and express the human Z A1AT protein in liver tissue. The mice used in this study are from the progeny of Carlson and colleagues (transgenic line Z11.03). HuZ mice have been used as a tool to assess the effects of an exemplar compound of the invention on either increasing the circulating levels of Z A1AT in plasma or the effects of compound on the accumulation of Z A1AT polymers in the liver and associated liver pathology.

HuZ mice (n=4/group; male or female) with basal human Z A1AT plasma levels of between 200-600 µg/ml were treated with either vehicle or the compounds of Examples 1 or 17 at 5, 15 or 50 mg/kg twice a day by oral gavage for 14 consecutive days. Mice had access to food (standard mouse chow, SAFE diets) and water ad libitum. On study day 14, each mouse was dosed one hour prior to terminal procedures. Blood was taken from each mouse from the tail vein on pre-dosing days −12, −7 and −5, and dosing days 12, 13 and 14. Blood was collected into microvettes containing EDTA and plasma was prepared by centrifugation at 2700×g at 4° C. for 10 min. Plasma was aliquoted and stored at −80° C. for bioanalysis. Plasma samples from pre-dosing days −12, −7 and −5 were used for to determine mean basal levels of human Z A1AT for each mouse. Plasma samples collected on the last three dosing days of the study (days 12, 13 and 14) were used to determine the effect of the compound of Example 1 or 17 on human Z A1AT secretion by measuring human Z A1AT levels and comparing to basal levels for each mouse. Human Z A1AT levels in mouse plasma samples were measured by ELISA (Human Serpin A1/$\alpha_1$ antitrypsin duo set ELISA, R& D Systems, DY1268) per manufacturer's instructions.

Briefly, a 96 well plate was coated with human A1AT capture antibody overnight at room temperature (1:180 dilution from stock, 100 μl final volume/well). The capture antibody was then removed and wells washed three times with 300 μl wash buffer (0.05% Tween 20 in PBS) and then 200 μl reagent diluent (25% Tween 20 in PBS) was incubated in each well for 1 h at room temperature. Diluted samples, standards (125, 250, 500, 1000, 2000, 4000 and 8000 pg/ml A1AT) or blanks were then added to each well in duplicate and the plates were covered with a plate sealer and left at room temperature for 2 h. At the end of the sample incubation step, samples were removed and all wells washed as previously and 100 μl detection antibody (1:180 dilution from stock) was added to each well and incubated for a further 2 h at room temperature. Following incubation with detection antibody, supernatant was removed and wells were washed as previously and 100 μl streptavidin-HRP solution (1:200 dilution from stock) was added to each well for 20 min in the dark. After which, 50 μl stop solution (2M $H_2SO_4$) was added and optical density (OD) of each well was read at 450 nm with 570 nm blank subtracted from each well using a microplate reader. A 4 parameter logistic curve was constructed using GraphPad Prism 7 and A1AT concentrations were determined in each sample by interpolation from a standard curve and multiplying by the appropriate dilution factor.

Results

The effect of the compound of Example 1 or 17 on circulating levels of human Z A1AT was assessed in the huZ mouse model.

The compounds of Example 1 and 17 stimulated secretion of human Z A1AT compared to baseline levels in huZ mice. FIG. 1 shows the data at each treatment dose for the compound of Example 17.

The invention claimed is:

1. A method of inducing Z A1AT secretion in a subject in need thereof, comprising administering to the subject a compound represented by the structure:

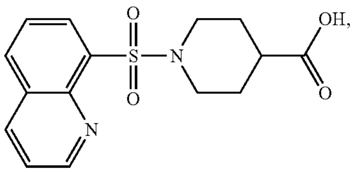

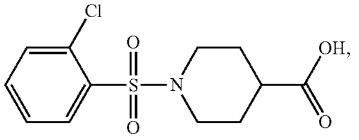

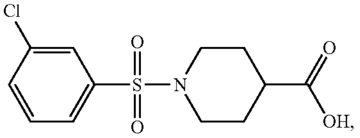

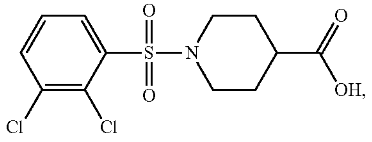

-continued

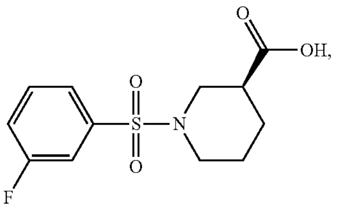

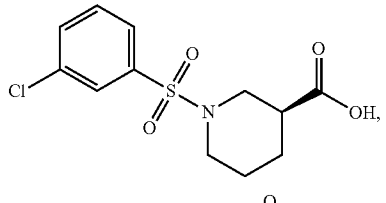

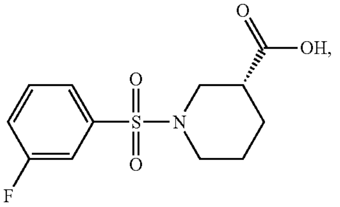 [SMILES: O=C(O)[C@@H]1CCCN(S(=O)(=O)c2cccc(F)c2)C1]

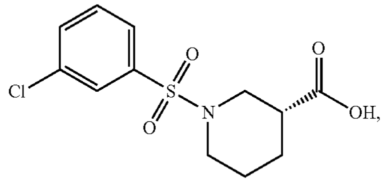 [SMILES: O=C(O)[C@@H]1CCCN(S(=O)(=O)c2cccc(Cl)c2)C1]

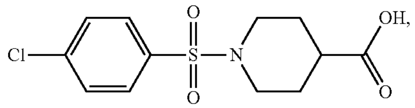

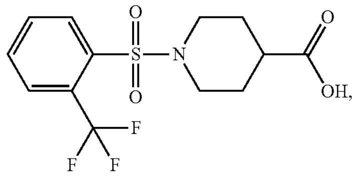

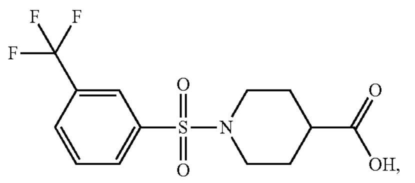

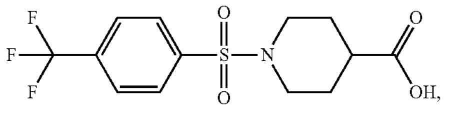

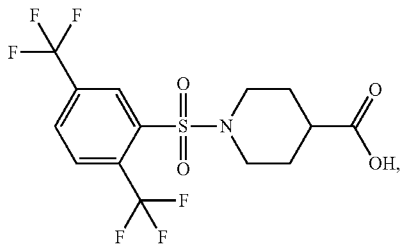

-continued
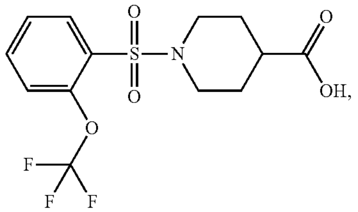
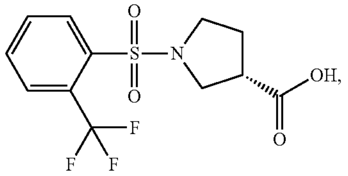
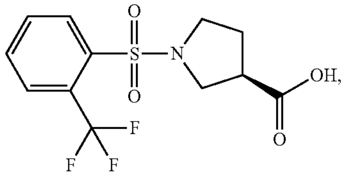
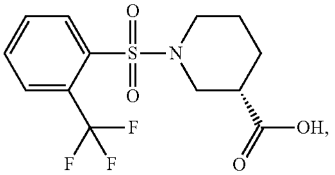 [SMILES: O=C(O)[C@H]1CCCN(S(=O)(=O)c2ccccc2C(F)(F)F)C1]
or
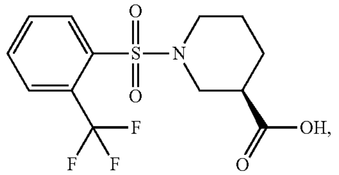
or a pharmaceutically acceptable salt of any one thereof.
2. A method of treating $\alpha_1$-antitrypsin deficiency (AATD), in a subject in need thereof, comprising administering to the subject a compound represented by the structure:
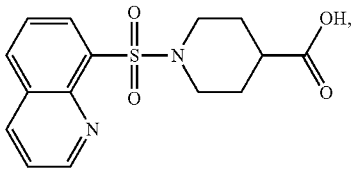
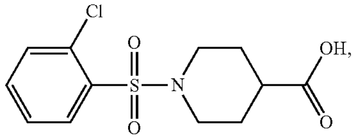
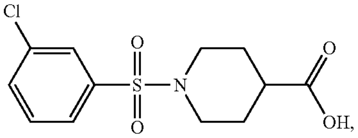
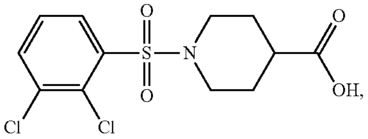
-continued
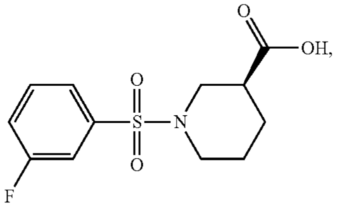
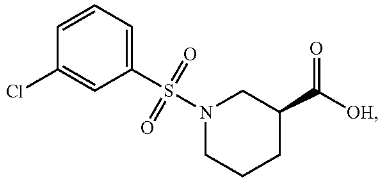
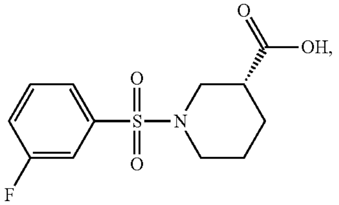
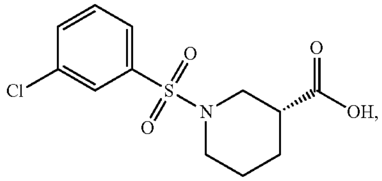
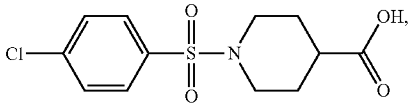
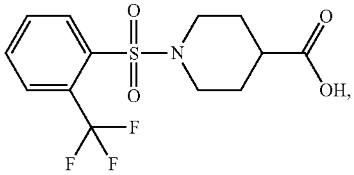
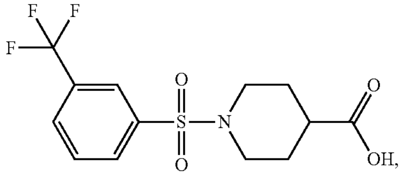
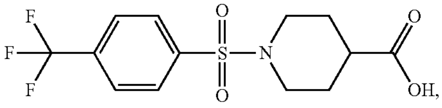
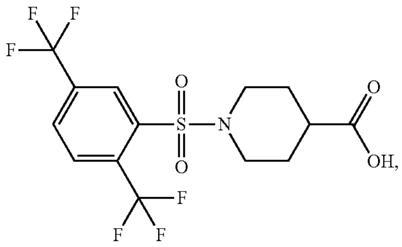

-continued
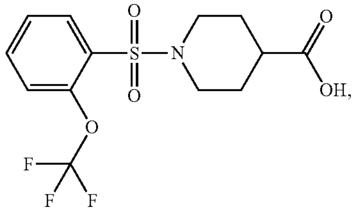
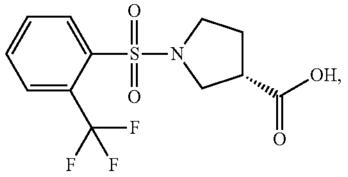
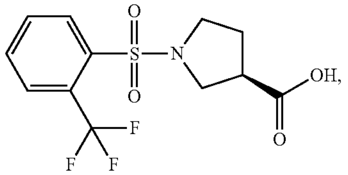
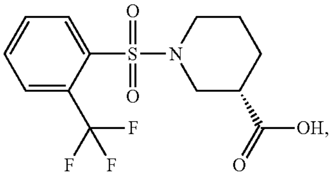
or
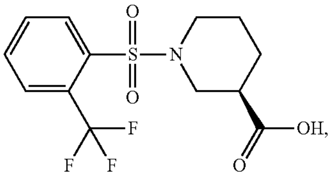
or a pharmaceutically acceptable salt of any one thereof.
3. The method of claim 1, wherein the method comprises administering a mixture of enantiomers selected from (a), (b), (c), or (d):
(a)
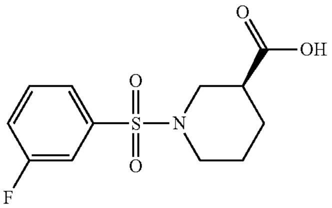
and
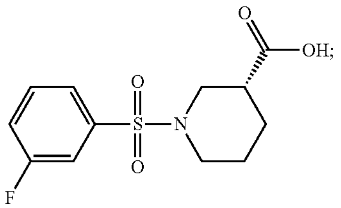
-continued
(b)
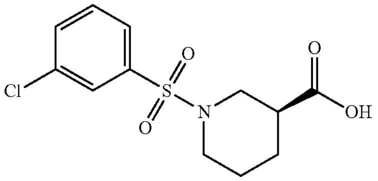
and
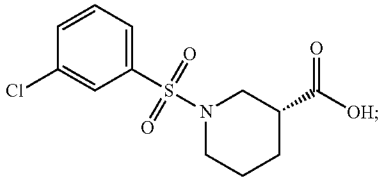
(c)
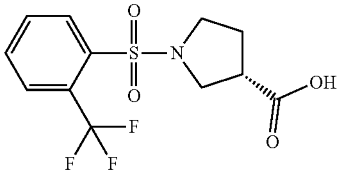
and
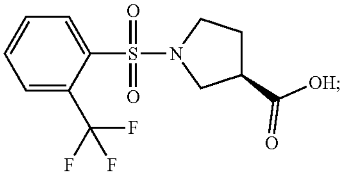
or
(d)
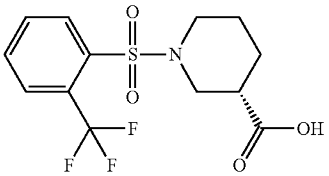
and
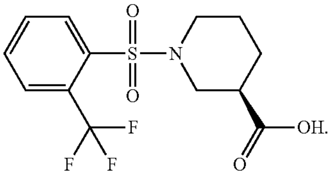
4. The method of claim 1, wherein the compound is represented by:
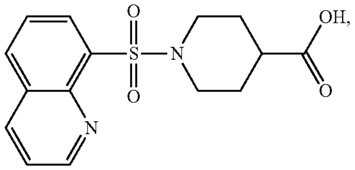
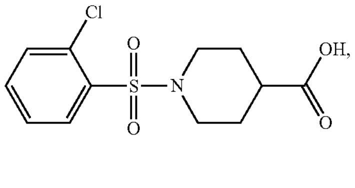

-continued
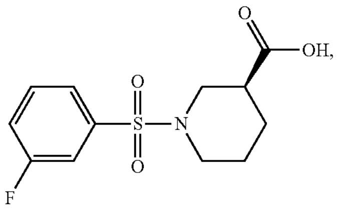
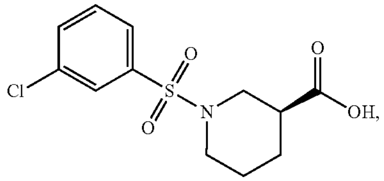
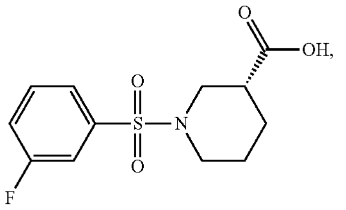 [SMILES: O=C(O)[C@@H]1CCCN(S(=O)(=O)c2cccc(F)c2)C1]
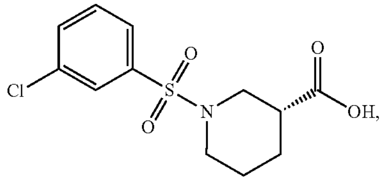
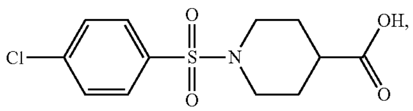
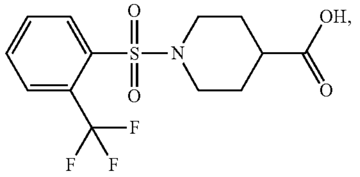
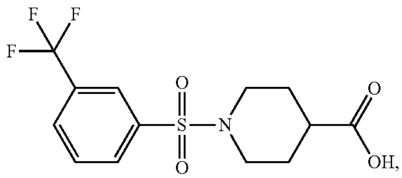
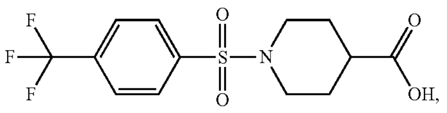
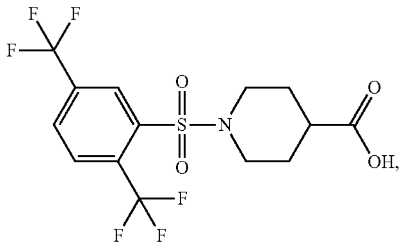
-continued
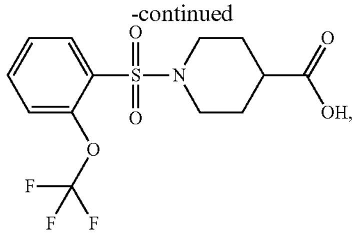
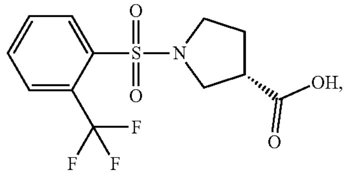
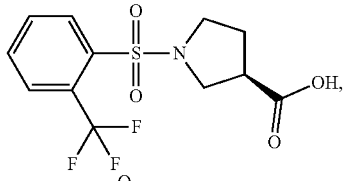
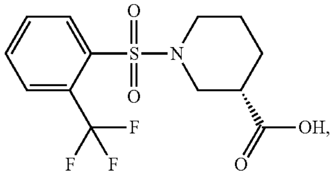
or
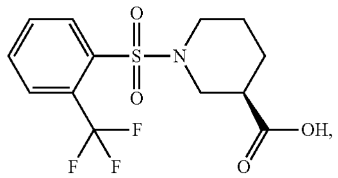
or a pharmaceutically acceptable salt of any one thereof.
5. The method of claim 4, wherein the compound is represented by:
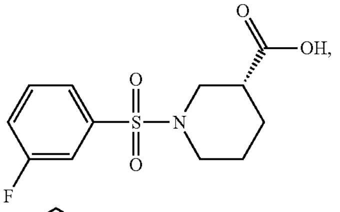
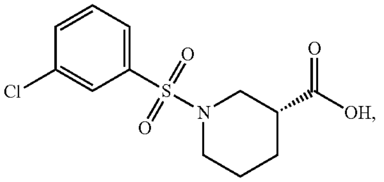
or
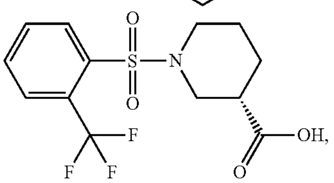
or a pharmaceutically acceptable salt of any one thereof.
6. The method of claim 5, wherein the compound is represented by:

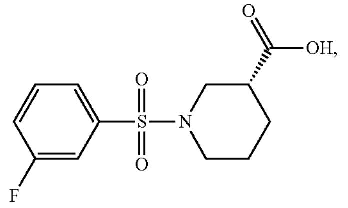

or a pharmaceutically acceptable salt thereof.

7. The method of claim 5, wherein the compound is represented by:

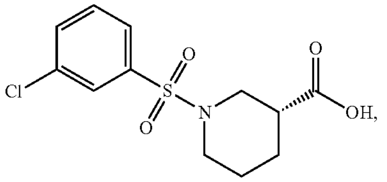

or a pharmaceutically acceptable salt thereof.

8. The method of claim 5, wherein the compound is represented by:

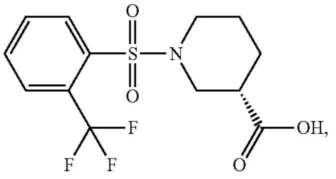

or a pharmaceutically acceptable salt thereof.

9. The method of claim 2, wherein the method comprises administering a mixture of enantiomers selected from (a), (b), (c), or (d):

(a)

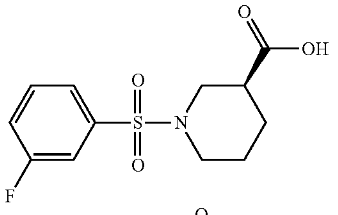

and

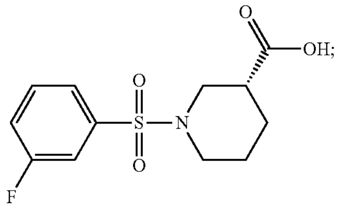

(b)

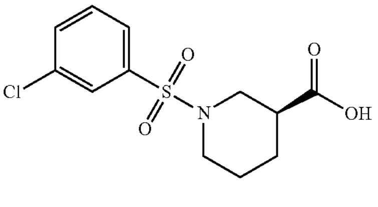

and

-continued

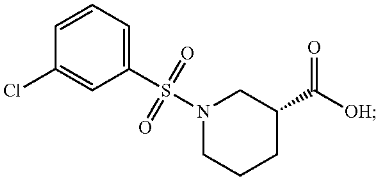 [SMILES: O=C(O)[C@@H]1CCCN(S(=O)(=O)c2cccc(Cl)c2)C1]

(c)

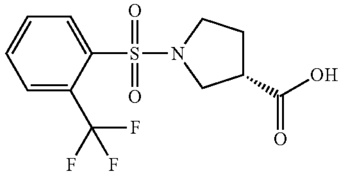

and

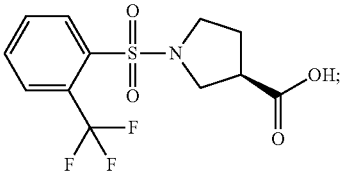

or (d)

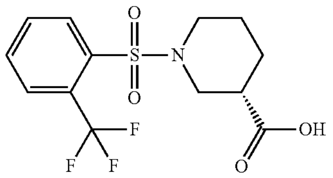

and

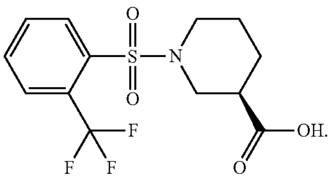

10. The method of claim 2, wherein the compound is represented by:

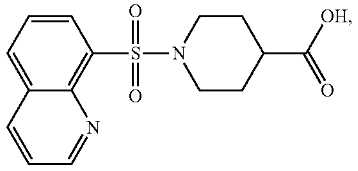

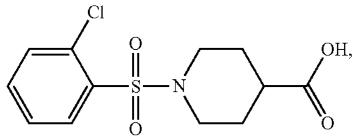

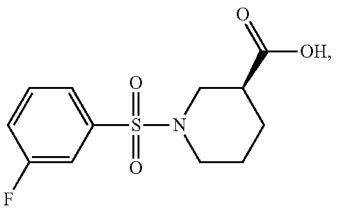

-continued
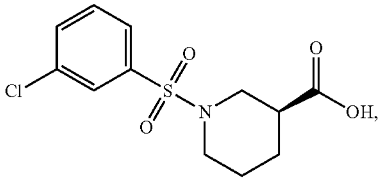
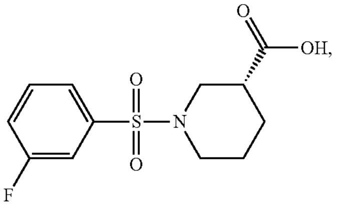
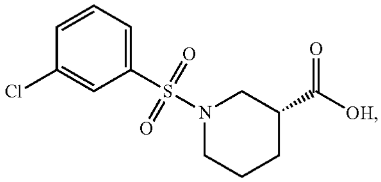
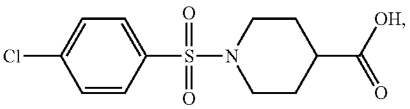
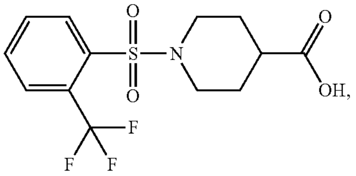
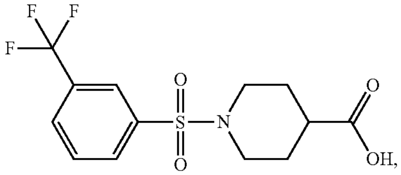
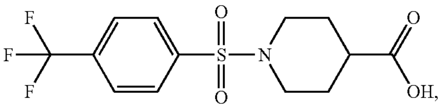
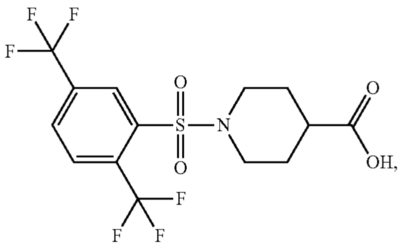
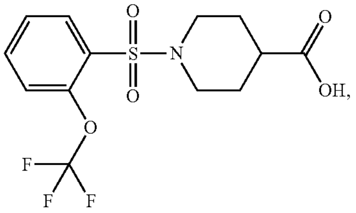
-continued
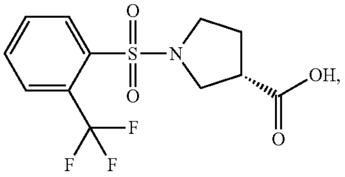
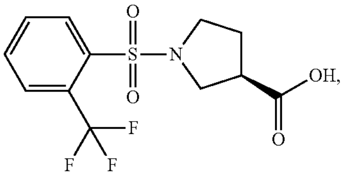
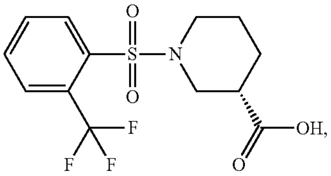
or
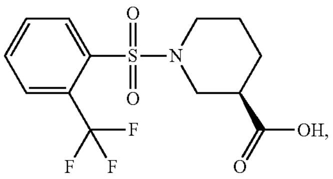
or a pharmaceutically acceptable salt of any one thereof.
11. The method of claim 10, wherein the compound is represented by:
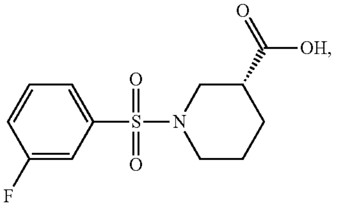
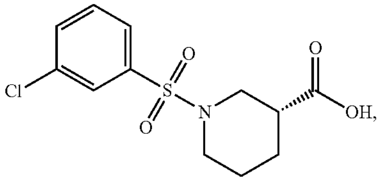
or
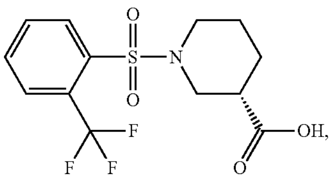
or a pharmaceutically acceptable salt of any one thereof.
12. The method of claim 11, wherein the compound is represented by:

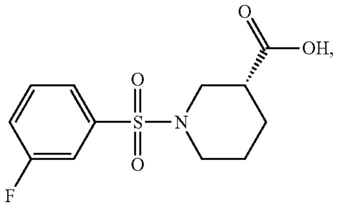

or a pharmaceutically acceptable salt thereof.

13. The method of claim 11, wherein the compound is represented by:

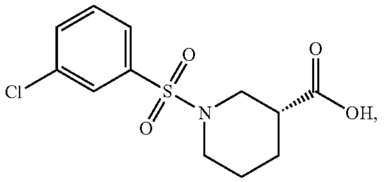

or a pharmaceutically acceptable salt thereof.

14. The method of claim 11, wherein the compound is represented by:

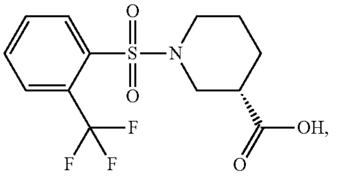 [SMILES: O=C(O)[C@H]1CCCN(S(=O)(=O)c2ccccc2C(F)(F)F)C1]

or a pharmaceutically acceptable salt thereof.

15. The method of claim 2, wherein the administering increases levels of Z A1AT in the subject.

16. The method of claim 15, wherein the administering does not affect the levels of wild type (M) A1AT in the subject.

17. The method of claim 15, wherein the administering does not affect the Siiyama variant of A1AT in the subject.

* * * * *